US012786592B2

(12) United States Patent
Osawa

(10) Patent No.: US 12,786,592 B2
(45) Date of Patent: Nov. 3, 2026

(54) IMAGING DEVICE, ENDOSCOPE SYSTEM, AND SIGNAL-PROCESSING METHOD

(71) Applicant: OLYMPUS MEDICAL SYSTEMS CORP., Hachioji (JP)

(72) Inventor: Masato Osawa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 180 days.

(21) Appl. No.: 18/402,017

(22) Filed: Jan. 2, 2024

(65) Prior Publication Data

US 2024/0251186 A1 Jul. 25, 2024

Related U.S. Application Data

(60) Provisional application No. 63/481,036, filed on Jan. 23, 2023.

(51) Int. Cl.

| | |
|---|---|
| ***H04N 25/772*** | (2023.01) |
| ***A61B 1/00*** | (2006.01) |
| ***H04N 23/50*** | (2023.01) |
| ***H04N 25/616*** | (2023.01) |
| ***H04N 25/76*** | (2023.01) |
| ***H04N 25/78*** | (2023.01) |

(52) U.S. Cl.

CPC ....... *H04N 25/772* (2023.01); *A61B 1/00009* (2013.01); *H04N 23/555* (2023.01); *H04N 25/616* (2023.01); *H04N 25/7795* (2023.01); *H04N 25/78* (2023.01)

(58) Field of Classification Search

CPC .................................................... H04N 25/616

See application file for complete search history.

(56) References Cited

U.S. PATENT DOCUMENTS

| | | | | |
|---|---|---|---|---|
| 2003/0214597 A1* | 11/2003 | Nam | H04N 25/633 348/308 |
| 2005/0168529 A1* | 8/2005 | Miyakawa | B41J 2/1433 347/45 |
| 2006/0012698 A1* | 1/2006 | Nitta | H04N 25/78 348/E3.018 |

(Continued)

FOREIGN PATENT DOCUMENTS

| | | | |
|---|---|---|---|
| EP | 2989962 A1 * | 3/2016 | H04N 25/71 |
| EP | 3203726 A1 * | 8/2017 | H04N 23/555 |

(Continued)

*Primary Examiner* — David N Werner

(74) *Attorney, Agent, or Firm* — WHDA, LLP

(57) ABSTRACT

An imaging device includes pixels, a sampling circuit, a reference signal generation circuit, a comparator, a measurement circuit, and a voltage adjustment circuit. The sampling circuit is configured to sample an analog signal. The comparator is configured to compare a voltage of the analog signal with a voltage of the reference signal. The reference signal generation circuit is configured to generate the reference signal that has a first voltage in a first period and has a second voltage in a second period. The measurement circuit is configured to measure the length of a period until the voltage of the analog signal and the voltage of the reference signal match each other. The voltage adjustment circuit is configured to adjust an analog voltage provided to the reference signal generation circuit such that a value of the first voltage nears a value of the second voltage.

9 Claims, 11 Drawing Sheets

(56) References Cited

U.S. PATENT DOCUMENTS

2009/0310001 A1* 12/2009 Masuyama ............ H04N 25/70
348/300
2011/0019047 A1* 1/2011 Suzuki ................. H04N 25/616
348/E5.091
2011/0114827 A1* 5/2011 Yamaoka ............... H03K 4/026
250/214 R
2011/0242381 A1* 10/2011 Sakakibara ............ H04N 25/65
348/301
2012/0006974 A1* 1/2012 Egawa ................. H04N 25/767
250/208.1
2012/0261552 A1* 10/2012 Ikeda ..................... H04N 25/78
250/208.1
2013/0026343 A1* 1/2013 Saito ...................... H04N 25/60
250/208.1
2013/0088292 A1* 4/2013 Maehashi ........... H03F 3/45475
330/124 R
2014/0252208 A1* 9/2014 Fujinaka .............. H04N 25/618
250/208.1
2016/0014363 A1* 1/2016 Kito ..................... H04N 25/617
348/308
2016/0028974 A1* 1/2016 Guidash ............... H04N 25/616
348/294
2016/0213238 A1* 7/2016 Adachi .............. A61B 1/00006
2016/0301883 A1* 10/2016 Kim ..................... H04N 25/616
2016/0313238 A1* 10/2016 Ochi .................... G01N 21/359
2016/0330387 A1* 11/2016 Hwang .................... H03K 4/90
2017/0195601 A1* 7/2017 Yun ......................... G05F 3/262
2018/0035868 A1* 2/2018 Saito ................ A61B 1/000095
2018/0227476 A1* 8/2018 Kobayashi ........... H04N 25/531
2019/0124285 A1* 4/2019 Otaka .................. H04N 25/575
2019/0260385 A1* 8/2019 Niwa ....................... H03M 1/12
2019/0305792 A1* 10/2019 Hasegawa .............. H04N 25/76
2019/0320877 A1* 10/2019 Sakai ..................... A61B 1/063
2020/0260037 A1* 8/2020 Cho .................... H03M 1/0697
2020/0357975 A1* 11/2020 Gumann ................ H05K 1/183
2022/0174230 A1* 6/2022 Kim ........................ H04N 25/78
2022/0394203 A1* 12/2022 Matsuura ............. H04N 23/741
2022/0409009 A1* 12/2022 Yamamura ......... A61B 1/00006
2023/0179890 A1* 6/2023 Kobayashi ........... H04N 25/767
2023/0225600 A1* 7/2023 Tani ................... A61B 1/00006
600/118
2023/0232131 A1* 7/2023 Ogawa ................... A61B 1/045
348/76
2023/0247328 A1* 8/2023 Nakamoto .............. H03M 1/38
348/300
2024/0323554 A1* 9/2024 Tamaki .................. H04N 25/78
2025/0350862 A1* 11/2025 Matsuura ............... H04N 25/60

FOREIGN PATENT DOCUMENTS

JP 2009-89050 A 4/2009
JP 2012-222563 A 11/2012
JP 2015035637 A * 2/2015 ............. H04N 25/46
JP 2015-136016 A 7/2015
JP 7189173 B2 * 12/2022

* cited by examiner

IMAGING DEVICE, ENDOSCOPE SYSTEM, AND SIGNAL-PROCESSING METHOD

Priority is claimed on U.S. Provisional Patent Application No. 63/481,036, filed on Jan. 23, 2023, the content of which is incorporated herein by reference.

BACKGROUND OF THE INVENTION

Field of the Invention

The present invention relates to an imaging device, an endoscope system, and a signal-processing method.

Description of Related Art

Column-parallel analog-to-digital converters (ADCs) are considered in order to reduce the area of image sensors. For example, such column-parallel ADCs are disclosed in Japanese Unexamined Patent Application, First Publication No. 2009-089050, in Japanese Unexamined Patent Application, First Publication No. 2015-136016, and in Japanese Unexamined Patent Application, First Publication No. 2012-222563. In an image sensor using a column-parallel ADC, one AD converter processes pixel signals generated in pixels of two or more columns. The AD converter includes a reference signal generation circuit, a comparator, and a counter.

The reference signal generation circuit generates a reference signal (ramp signal) having a voltage that gradually decreases or increases by using a predetermined analog voltage. The comparator compares the voltage of the pixel signal with the voltage of the reference signal. The counter measures the length of time until the voltage of the pixel signal and the voltage of the reference signal match each other. The length of time measured by the counter corresponds to a digital value of the pixel signal.

SUMMARY OF THE INVENTION

According to a first aspect of the present invention, an imaging device includes pixels, a sampling circuit, a reference signal generation circuit, a comparator, a measurement circuit, and a voltage adjustment circuit. The pixels are disposed in a matrix shape having two or more rows and two or more columns. The sampling circuit is configured to sample an analog signal output from each of the pixels disposed in a multiple predetermined number of the columns in a sampling period. The reference signal generation circuit is configured to generate a reference signal having a voltage that gradually increases or decreases from a first timing by using an analog voltage in a reference signal generation period. The comparator is configured to execute comparison processing of comparing a voltage of the analog signal sampled by the sampling circuit with a voltage of the reference signal. The measurement circuit is configured to measure a length of a period from the first timing to a second timing at which the voltage of the analog signal and the voltage of the reference signal match each other. The sampling circuit is configured to sample the predetermined number of the analog signals in the sampling period. The comparator is configured to compare the voltage of each of the analog signals with the voltage of the reference signal so as to execute the comparison processing. The reference signal generation circuit is configured to generate the reference signal having a first voltage at the first timing of a first period that is the reference signal generation period immediately after the sampling period. The reference signal generation circuit is configured to generate the reference signal having a second voltage at the first timing of a second period that is the reference signal generation period after the first period. The voltage adjustment circuit is configured to adjust the analog voltage provided to the reference signal generation circuit before the first timing of the first period such that a value of the first voltage nears a value of the second voltage.

According to a second aspect of the present invention, in the first aspect, the voltage adjustment circuit may be configured to short-circuit, at a third timing before the first period, the reference signal generation circuit and a voltage terminal to which a different voltage from the analog voltage is provided. The voltage adjustment circuit may be configured to cancel a short circuit between the reference signal generation circuit and the voltage terminal at a fourth timing that occurs after the third timing and before the first period so as to adjust the analog voltage.

According to a third aspect of the present invention, in the second aspect, the reference signal generation circuit may include a capacitance element configured to hold the first voltage and the second voltage. The voltage adjustment circuit may be configured to short-circuit the capacitance element and the voltage terminal at the third timing and may be configured to cancel a short circuit between the capacitance element and the voltage terminal at the fourth timing.

According to a fourth aspect of the present invention, in the third aspect, the third timing may occur after the pixels are reset and before the first timing of the first period.

According to a fifth aspect of the present invention, in the first aspect, the voltage adjustment circuit may be configured to adjust the analog voltage by consuming the same amount of current as an amount of current consumed by the measurement circuit before the first period.

According to a sixth aspect of the present invention, in the fifth aspect, the voltage adjustment circuit and the reference signal generation circuit may be connected in parallel to a voltage terminal to which the analog voltage is provided.

According to a seventh aspect of the present invention, in the first aspect, the reference signal generation circuit may be configured to output the reference signal having a third voltage in a third period. The third period may be included in the sampling period and may occur before a period during which the voltage adjustment circuit adjusts the analog voltage. A difference between the first voltage and the second voltage may be less than a difference between the third voltage and the second voltage.

According to an eighth aspect of the present invention, an endoscope system includes a scope and the imaging device. The scope is to be inserted into a living body. The imaging device is disposed in a distal end of the scope.

According to a ninth aspect of the present invention, a signal-processing method includes a step in which a sampling circuit samples an analog signal output from each of pixels disposed in a multiple predetermined number of columns in a sampling period. The signal-processing method includes a step in which a reference signal generation circuit generates a reference signal having a voltage that gradually increases or decreases from a first timing by using an analog voltage in a reference signal generation period. The signal-processing method includes a step in which a comparator executes comparison processing of comparing a voltage of the analog signal sampled by the sampling circuit with a voltage of the reference signal. The signal-processing method includes a step in which a measurement circuit measures a length of a period from the first timing to a second timing at which the voltage of the analog signal and the voltage of the reference signal match each other. The signal-processing method includes a step in which a voltage adjustment circuit adjusts the analog voltage provided to the reference signal generation circuit. The step of sampling the analog signal includes sampling the predetermined number of the analog signals in the sampling period. The step of comparing the voltage of the analog signal with the voltage of the reference signal includes comparing the voltage of each of the analog signals with the voltage of the reference signal so as to execute the comparison processing. The step of generating the reference signal includes generating the reference signal having a first voltage at the first timing of a first period that is the reference signal generation period immediately after the sampling period and includes generating the reference signal having a second voltage at the first timing of a second period that is the reference signal generation period after the first period. The step of adjusting the analog voltage includes adjusting the analog voltage provided to the reference signal generation circuit before the first timing of the first period such that a value of the first voltage nears a value of the second voltage.

DETAILED DESCRIPTION OF THE INVENTION

Embodiments of the present invention will be described with reference to the drawings. Hereinafter, an example of an endoscope system including an imaging device will be described.

First Embodiment

Figure 1:
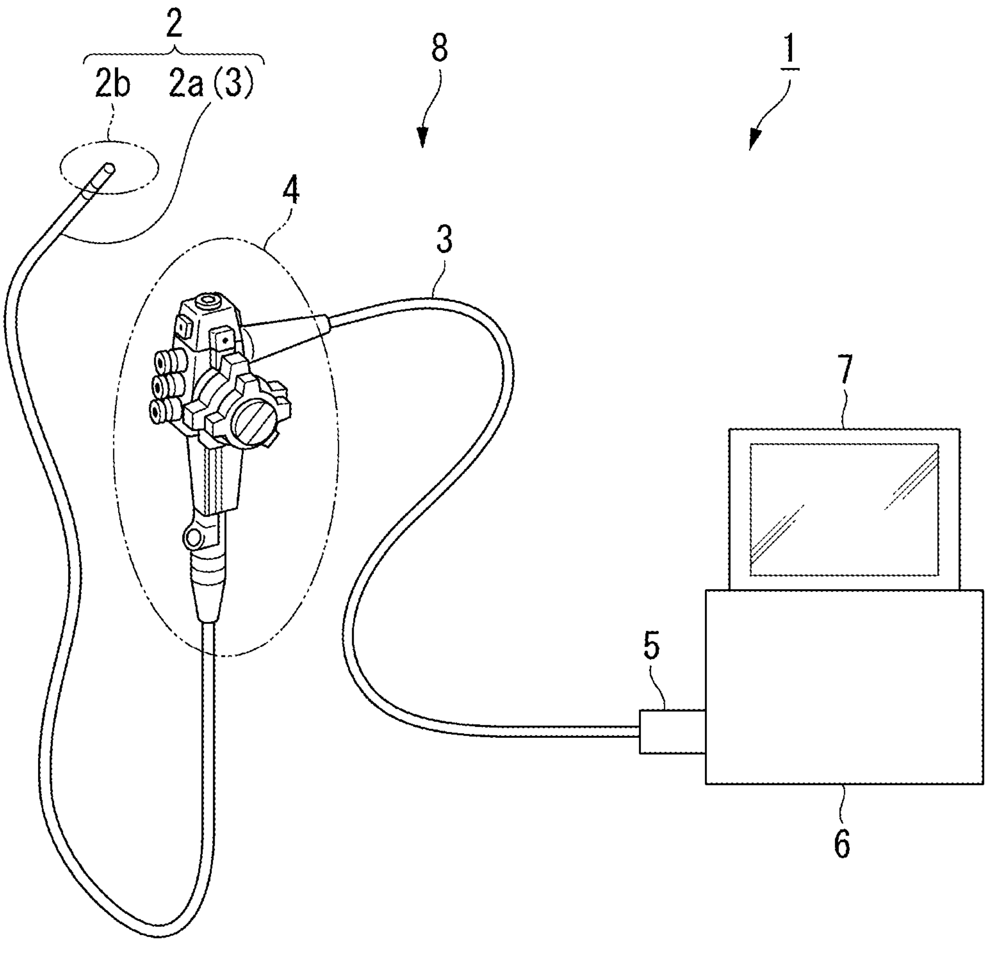
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a control unit 6, and a display device 7. The endoscope insertion unit 2, the transmission cable 3, the operation unit 4, and the connector unit 5 constitute a scope 8.

Figure 2:
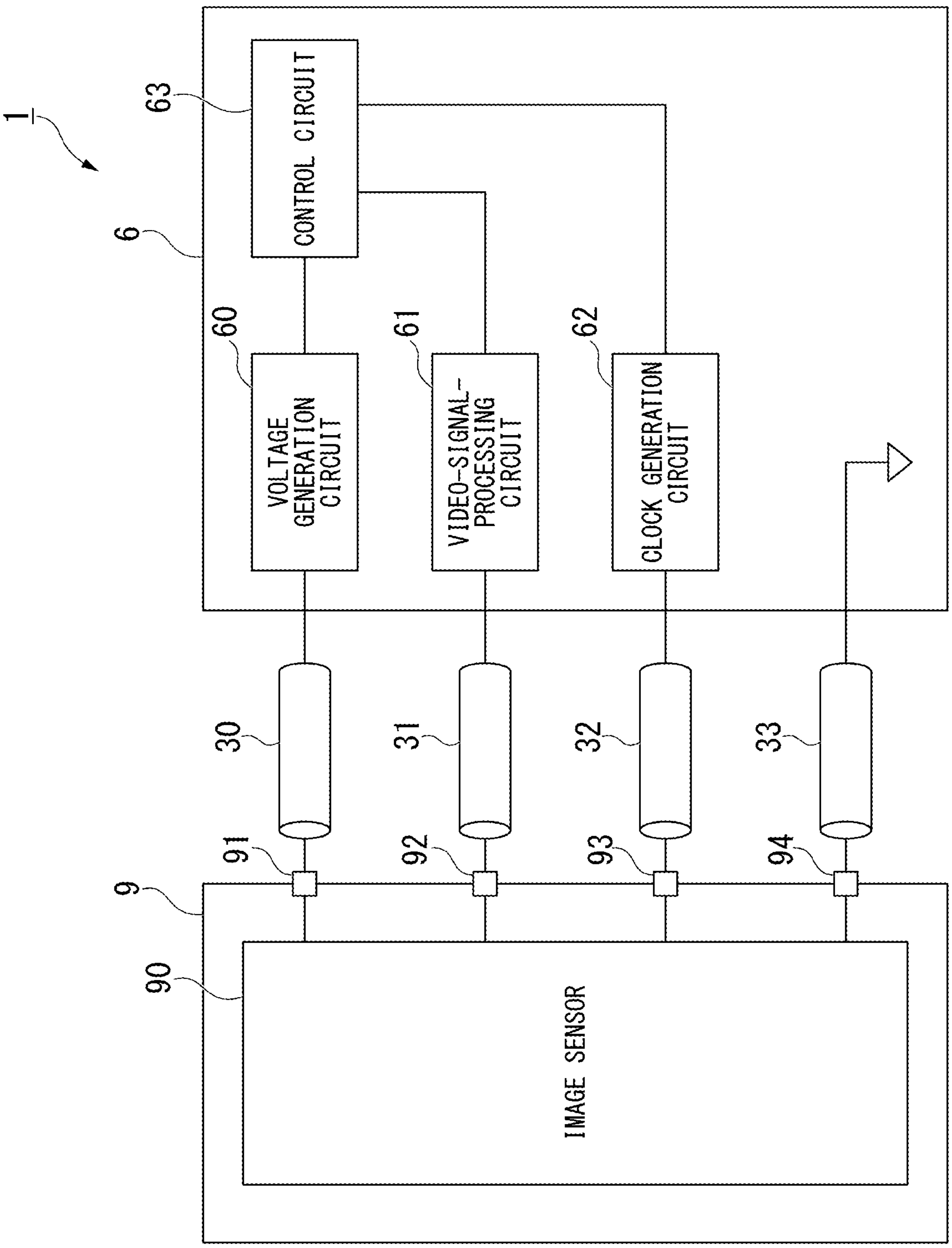
FIG. 2 is a block diagram showing a configuration of a camera unit and a control unit included in the endoscope system according to the first embodiment of the present invention.

The endoscope insertion unit 2 includes an insertion unit 2*a*. The insertion unit 2*a* is part of the transmission cable 3. The insertion unit 2*a* is to be inserted inside a living body, which is a subject. The endoscope insertion unit 2 generates a video signal by imaging the inside of the subject. The endoscope insertion unit 2 outputs the generated video signal to the control unit 6. A camera unit 9 shown in FIG. 2 is disposed in a distal end 2*b* of the insertion unit 2*a*. In the insertion unit 2*a*, the operation unit 4 is connected to the proximal end part opposite the distal end 2*b*. The operation unit 4 receives various operations for the endoscope insertion unit 2 from a user.

The transmission cable 3 connects the camera unit 9 and the connector unit 5. The video signal generated by the camera unit 9 is output to the connector unit 5 via the transmission cable 3.

The connector unit 5 is connected to the endoscope insertion unit 2 and the control unit 6. The connector unit 5 performs predetermined processing on the video signal output from the endoscope insertion unit 2. The connector unit 5 outputs the video signal to the control unit 6.

The control unit 6 performs image processing on the video signal output from the connector unit 5. Furthermore, the control unit 6 centrally controls the entire endoscope system 1.

The display device 7 displays a video based on the video signal processed by the control unit 6. In addition, the display device 7 displays various kinds of information related to the endoscope system 1.

The endoscope system 1 includes the camera unit 9 and the control unit 6 shown in FIG. 2. FIG. 2 shows a configuration of the camera unit 9 and the control unit 6. The camera unit 9 is an imaging device. The camera unit 9 is disposed in the distal end 2*b* of the scope 8. The operation unit 4, the connector unit 5, and the display device 7 are not shown in FIG. 2. The transmission cable 3 shown in FIG. 1 includes a power source line 30, a video signal line 31, a clock signal line 32, and a ground line 33 shown in FIG. 2. The camera unit 9 and the control unit 6 are connected to each other by the power source line 30, the video signal line 31, the clock signal line 32, and the ground line 33.

The endoscope system 1 includes a light source device that generates illumination light emitted to the subject. The light source device is not shown in FIG. 2.

The camera unit 9 includes an image sensor 90, a power source terminal 91, a video terminal 92, a clock terminal 93, and a ground terminal 94. The control unit 6 includes a voltage generation circuit 60, a video-signal-processing circuit 61, a clock generation circuit 62, and a control circuit 63.

For example, the voltage generation circuit 60 is a voltage regulator. The voltage generation circuit 60 generates a power source voltage that is a direct-current (DC) voltage and outputs the power source voltage to the power source line 30. The power source line 30 is a signal line disposed in the transmission cable 3. The power source line 30 transfers the power source voltage to the camera unit 9.

The power source terminal 91 is connected to the power source line 30. The power source voltage transferred by the power source line 30 is input to the power source terminal 91. The power source terminal 91 outputs the power source voltage to the image sensor 90. The image sensor 90 generates a video signal based on the power source voltage and outputs the video signal to the video terminal 92.

The video terminal 92 is connected to the video signal line 31. The video terminal 92 outputs the video signal to the video signal line 31. The video signal line 31 is a signal line disposed in the transmission cable 3. The video signal line 31 transfers the video signal to the control unit 6.

The video-signal-processing circuit 61 receives the video signal transferred by the video signal line 31. The video-signal-processing circuit 61 performs predetermined signal processing on the video signal and outputs the video signal to the display device 7.

The clock generation circuit 62 generates a clock signal (master clock) and outputs the clock signal to the clock signal line 32. The clock signal line 32 is a signal line disposed in the transmission cable 3. The clock signal line 32 transfers the clock signal to the camera unit 9.

The clock terminal 93 is connected to the clock signal line 32. The clock signal transferred by the clock signal line 32 is input to the clock terminal 93. The clock terminal 93 outputs the clock signal to the image sensor 90. The image sensor 90 operates at timings in accordance with the clock signal.

The ground terminal 94 is connected to the ground line 33. The ground line 33 is a signal line disposed in the transmission cable 3. The ground line 33 is a conductive line and keeps the ground level of the control unit 6 and the ground level of the image sensor 90 almost the same.

The control circuit 63 controls the operations of the voltage generation circuit 60, the video-signal-processing circuit 61, and the clock generation circuit 62.

Figure 3:
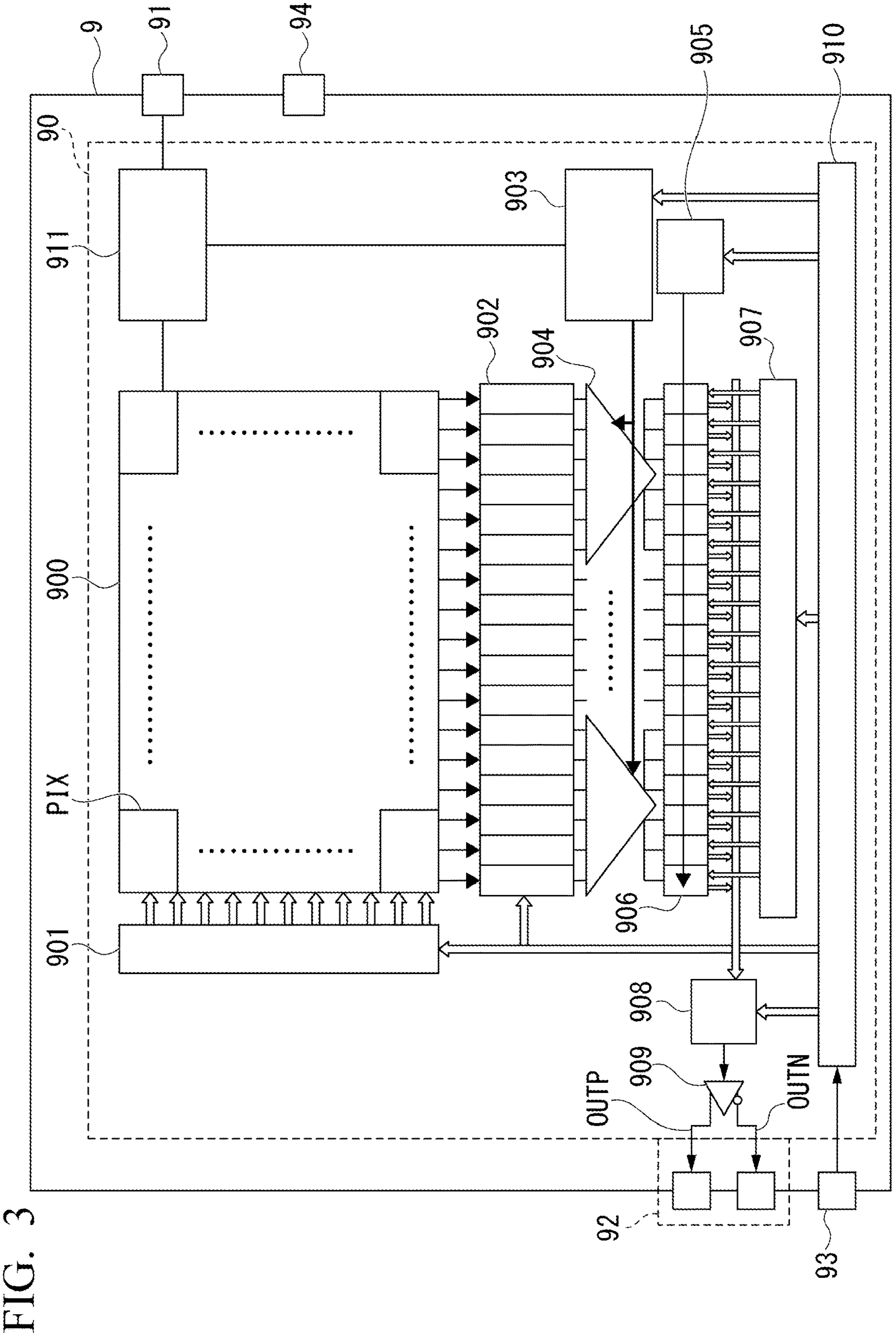
FIG. 3 is a block diagram showing a configuration of an image sensor included in the endoscope system according to the first embodiment of the present invention.

FIG. 3 shows a configuration of the image sensor 90. The image sensor 90 includes a pixel unit 900, a reading control unit 901, a reading circuit 902, a reference signal generation circuit 903, a comparator 904, a counter 905, a latch circuit 906, a horizontal reading control unit 907, a digital signal-processing unit 908, a signal output unit 909, a timing generator (TG) 910, and a voltage generation circuit 911.

A schematic configuration of the image sensor 90 will be described. The pixel unit 900 includes pixels PIX disposed in a matrix shape having two or more rows and two or more columns. The reading circuit 902 (sampling circuit) samples an analog signal output from each of the pixels PIX disposed in a predetermined number of the columns in a sampling period. The predetermined number is at least two. The reference signal generation circuit 903 generates a reference signal having a voltage that gradually increases or decreases from a first timing by using an analog voltage in a reference signal generation period. The comparator 904 executes comparison processing of comparing the voltage of the analog signal sampled by the reading circuit 902 with the voltage of the reference signal. The counter 905 (measurement circuit) is used to measure the length of a period from the first timing to a second timing at which the voltage of the analog signal and the voltage of the reference signal match each other.

The reading circuit 902 samples the predetermined number of the analog signals in the sampling period. The comparator 904 compares the voltage of each of the predetermined number of the analog signals with the voltage of the reference signal so as to execute the comparison processing the predetermined number of times. The reference signal generation circuit 903 generates the reference signal having a first voltage at the first timing of a first period that is the reference signal generation period immediately after the sampling period. The reference signal generation circuit 903 generates the reference signal having a second voltage at the first timing of a second period that is the reference signal generation period after the first period. The reference signal generation circuit 903 includes a voltage adjustment circuit. The voltage adjustment circuit adjusts the analog voltage provided to the reference signal generation circuit 903 before the first timing of the first period such that the value of the first voltage nears the value of the second voltage.

A detailed configuration of the image sensor 90 will be described. The pixel unit 900 includes four or more pixels PIX disposed in a matrix shape. The number of rows and the number of columns in an array (pixel array) of the four or more pixels PIX are two or more. The pixels PIX generate analog pixel signals in accordance with light incident thereon.

The power source voltage is output from the power source terminal 91 and is input to the image sensor 90. When the pixel PIX is reset by using a predetermined voltage generated in accordance with the power source voltage, the pixel PIX generates a first pixel signal. After the pixel PIX is reset, an electric charge is stored in the pixel PIX in accordance with the amount of light incident on the pixel PIX. The pixel PIX generates a second pixel signal in accordance with the electric charge.

The reading control unit 901 selects each row in the pixel array. Pixels PIX of the row selected by the reading control unit 901 output pixel signals.

The image sensor 90 includes two or more reading circuits 902. The number of the reading circuits 902 is the same as that of columns in the pixel array. The reading circuits 902 holds an analog signal corresponding to the difference between the first pixel signal and the second pixel signal output from the pixels PIX of each row.

The reference signal generation circuit 903 generates a reference signal in two or more reference signal generation periods after the sampling period. Hereinafter, an example in which the reference signal generation circuit 903 generates a reference signal having a voltage that gradually decreases will be described.

The image sensor 90 includes one or more comparators 904. At least two analog signals held by at least two reading circuits 902 are sequentially input to one comparator 904. Hereinafter, an example in which six analog signals held by six reading circuits 902 are sequentially input to one comparator 904 will be described. The number of analog signals input to one comparator 904 is not limited to six.

Six AD conversion periods (reference signal generation periods) follow the sampling period. The analog signal is input from each reading circuit 902 to the comparator 904 in each AD conversion period. The reference signal is input from the reference signal generation circuit 903 to the comparator 904 in each AD conversion period. The comparator 904 compares the voltage of the analog signal with the voltage of the reference signal in each AD conversion period. The comparator 904 outputs a comparison signal in accordance with a comparison result. The comparison signal has a high (H) voltage or a low (L) voltage. For example, the H voltage is the power source voltage, and the L voltage is a ground voltage. When the voltage of the analog signal and the voltage of the reference signal match each other, the voltage of the comparison signal changes.

The counter 905 stops the operation thereof in the sampling period. The counter 905 outputs a digital value indicating a measurement value of time in the AD conversion period. The digital value increases or decreases from an initial value as time passes.

The image sensor 90 includes as many of the latch circuits 906 as the reading circuits 902. The comparator 904 compares the voltage of the analog signal output from the reading circuit 902 of each column with the voltage of the reference signal and outputs the comparison signal to the latch circuit 906 of the column. When the voltage of the comparison signal change, the latch circuit 906 holds a digital value output from the counter 905. The digital value held by the latch circuit 906 indicates an AD conversion result of the analog signal.

The horizontal reading control unit 907 sequentially selects two or more latch circuits 906. The latch circuit 906 selected by the horizontal reading control unit 907 outputs the digital value to the digital signal-processing unit 908.

The digital signal-processing unit 908 performs digital signal processing on the digital value and outputs the digital value to the signal output unit 909. The signal output unit 909 converts the digital value to a differential signal and outputs the differential signal to the video terminal 92. The differential signal includes a first digital signal OUTP and a second digital signal OUTN.

The clock signal is output from the clock terminal 93 and is input to the TG 910. The TG 910 generates a timing signal based on the clock signal and outputs the timing signal to the reading control unit 901, the reading circuit 902, the reference signal generation circuit 903, the counter 905, the horizontal reading control unit 907, and the digital signal-processing unit 908. The timing signal specifies timings of the operation of each circuit.

The power source voltage is output from the power source terminal 91 and is input to the voltage generation circuit 911. The voltage generation circuit 911 generates an analog signal based on the power source voltage. For example, the analog voltage is higher than the ground voltage and is lower than the power source voltage.

Figure 4:
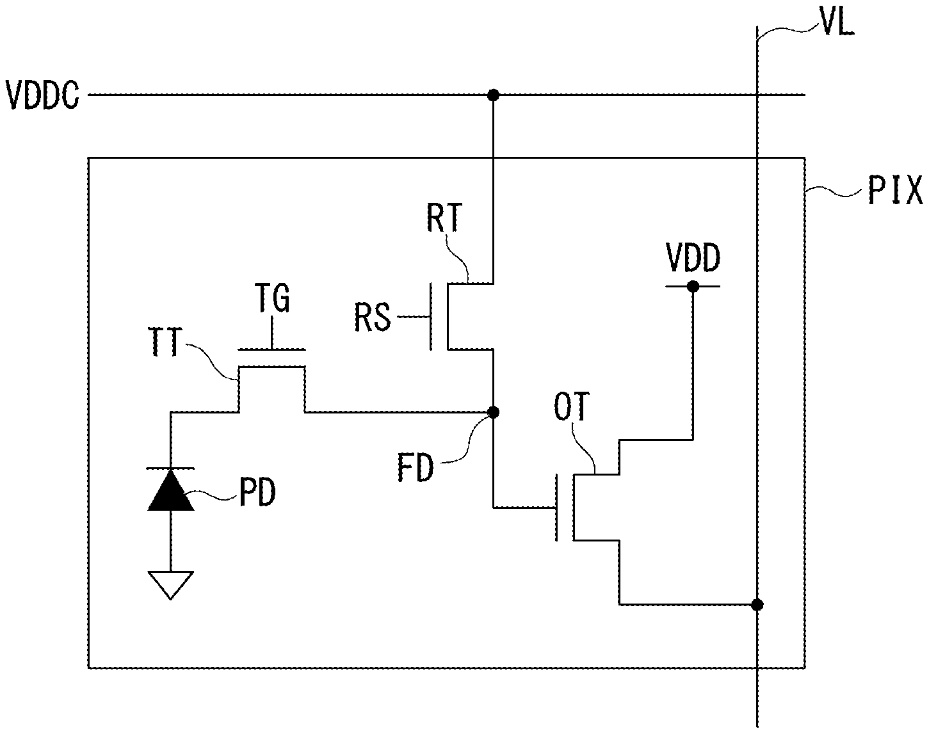
FIG. 4 is a diagram showing a configuration of a pixel in the image sensor included in the endoscope system according to the first embodiment of the present invention.

FIG. 4 shows a configuration of the pixel PIX. The pixel PIX includes a photoelectric conversion unit PD, a transfer transistor TT, a reset transistor RT, a charge storage portion FD, and an output transistor OT.

The reading control unit 901 generates a control signal VDDC, a control signal RS, and a control signal TG. The control signal VDDC, the control signal RS, and the control signal TG are input to the pixel PIX.

The photoelectric conversion unit PD is a photodiode. The photoelectric conversion unit PD generates an electric charge in accordance with the amount of light incident thereon.

The transfer transistor TT transfers the electric charge generated by the photoelectric conversion unit PD to the charge storage portion FD. The operation of the transfer transistor TT is controlled based on the control signal TG.

The charge storage portion FD is a floating diffusion. The charge storage portion FD stores the electric charge transferred by the transfer transistor TT.

The reset transistor RT resets the voltage of the charge storage portion FD to a voltage in accordance with the control signal VDDC. The operation of the reset transistor RT is controlled based on the control signal RS.

A power source voltage VDD is input to the drain terminal of the output transistor OT. The source terminal of the output transistor OT is connected to a vertical signal line VL. The gate terminal of the output transistor OT is connected to the charge storage portion FD. The output transistor OT outputs a pixel signal to the vertical signal line VL based on the voltage of the charge storage portion FD.

The vertical signal line VL is disposed for each column in the pixel array and extends in a vertical direction, that is, a column direction. The vertical signal line VL is connected to the pixel PIX of each column and the reading circuit 902. The vertical signal line VL transfers the pixel signal to the reading circuit 902.

Figure 5:
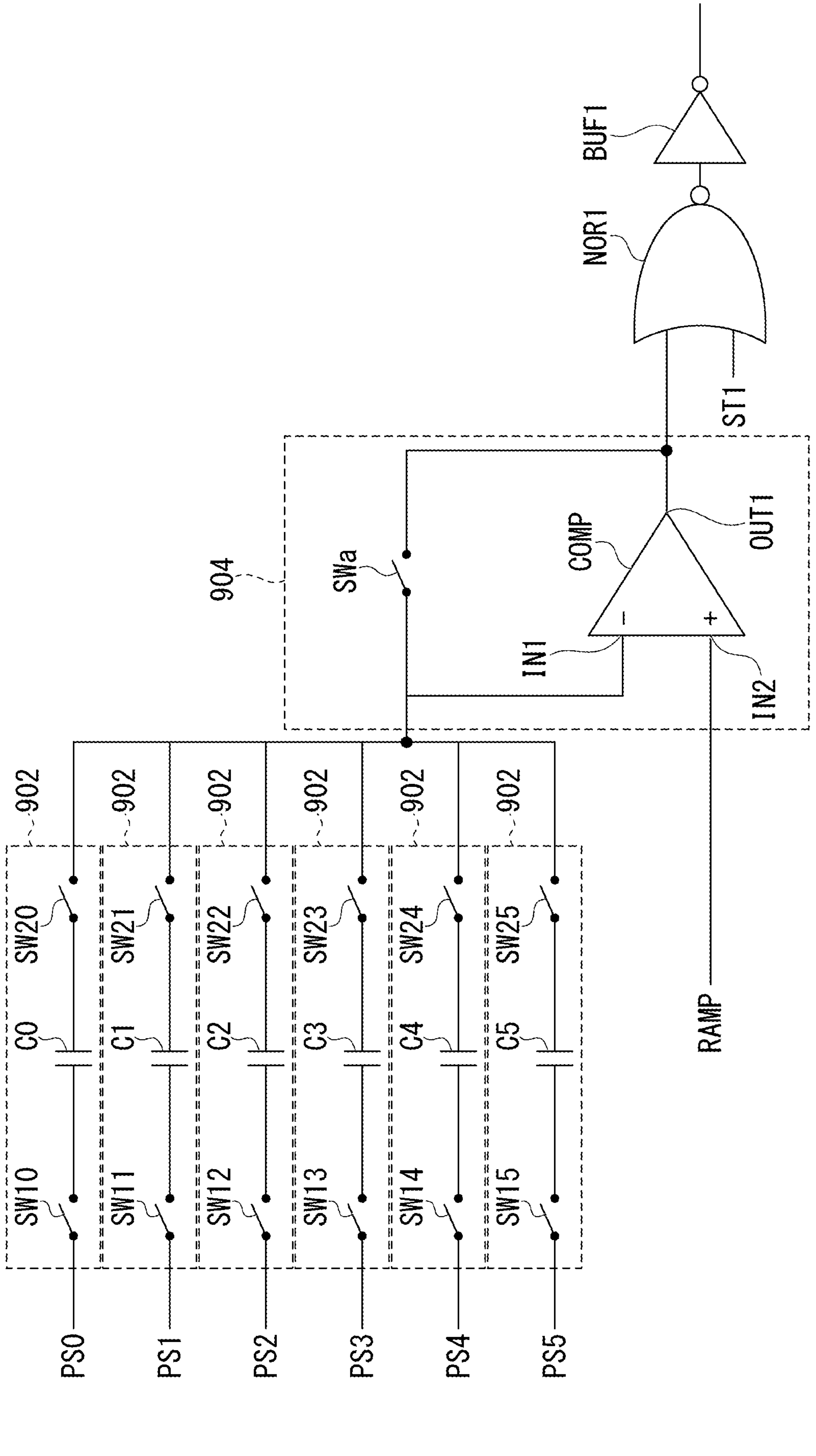
FIG. 5 is a diagram showing a configuration of a circuit including both a reading circuit and a comparator in the image sensor included in the endoscope system according to the first embodiment of the present invention.

FIG. 5 shows a configuration of a circuit including both the reading circuit 902 and the comparator 904. The circuit shown in FIG. 5 includes switches SW10 to SW15, capacitance elements C0 to C5, switches SW20 to SW25, a switch SWa, a comparison circuit COMP, a NOR circuit NOR1, and a buffer BUF1.

The state of each switch shown in FIG. 5 becomes either an ON state or an OFF state. Each switch can switch between the ON state and the OFF state.

A configuration of six reading circuits 902 is shown in FIG. 5. Each reading circuit 902 includes one of the switches SW10 to SW15, one of the capacitance elements C0 to C5, and one of the switches SW20 to SW25.

Pixel signals PSO to PS5 are output from the pixels PIX. Each of the pixel signals PSO to PS5 is a first pixel signal or a second pixel signal. The pixel signals PSO to PS5 are input to the six reading circuits 902.

One of the six reading circuits 902 includes the switch SW10, the capacitance element C0, and the switch SW20. The switch SW10 is connected to the vertical signal line VL shown in FIG. 4. When the state of the switch SW10 is the ON state, the pixel signal PSO is input to the capacitance element C0 via the switch SW10. The capacitance element C0 holds an analog signal corresponding to the first pixel signal, and then holds an analog signal corresponding to the difference between the first pixel signal and the second pixel signal. The configuration of the other five reading circuits 902 is the same as the above-described configuration.

The comparator 904 includes the switch SWa and the comparison circuit COMP. The comparison circuit COMP includes an inverting input terminal IN1, a non-inverting input terminal IN2, and an output terminal OUT1. When the state of the switch SW20 is the ON state, the analog signal held by the capacitance element C0 is input to the inverting input terminal IN1 via the switch SW20. The switch SWa is connected to the inverting input terminal IN1 and the output terminal OUT1.

A reference signal RAMP is generated by the reference signal generation circuit 903 and is input to the non-inverting input terminal IN2. When the state of the switch SWa is the OFF state, the comparison circuit COMP compares the voltage of the inverting input terminal IN1 with the voltage of the non-inverting input terminal IN2 and outputs a comparison signal in accordance with the comparison result.

The comparison signal is input to the NOR circuit NOR1. In addition, a start signal ST1 is output from the TG 910 and is input to the NOR circuit NOR1. The voltage of the start signal ST1 is the H voltage or the L voltage. When the voltage of the start signal ST1 is the H voltage, the NOR circuit NOR1 stops the output of the comparison signal. When the voltage of the start signal ST1 is the L voltage, the NOR circuit NOR1 outputs the comparison signal via the buffer BUF1.

Figure 6:
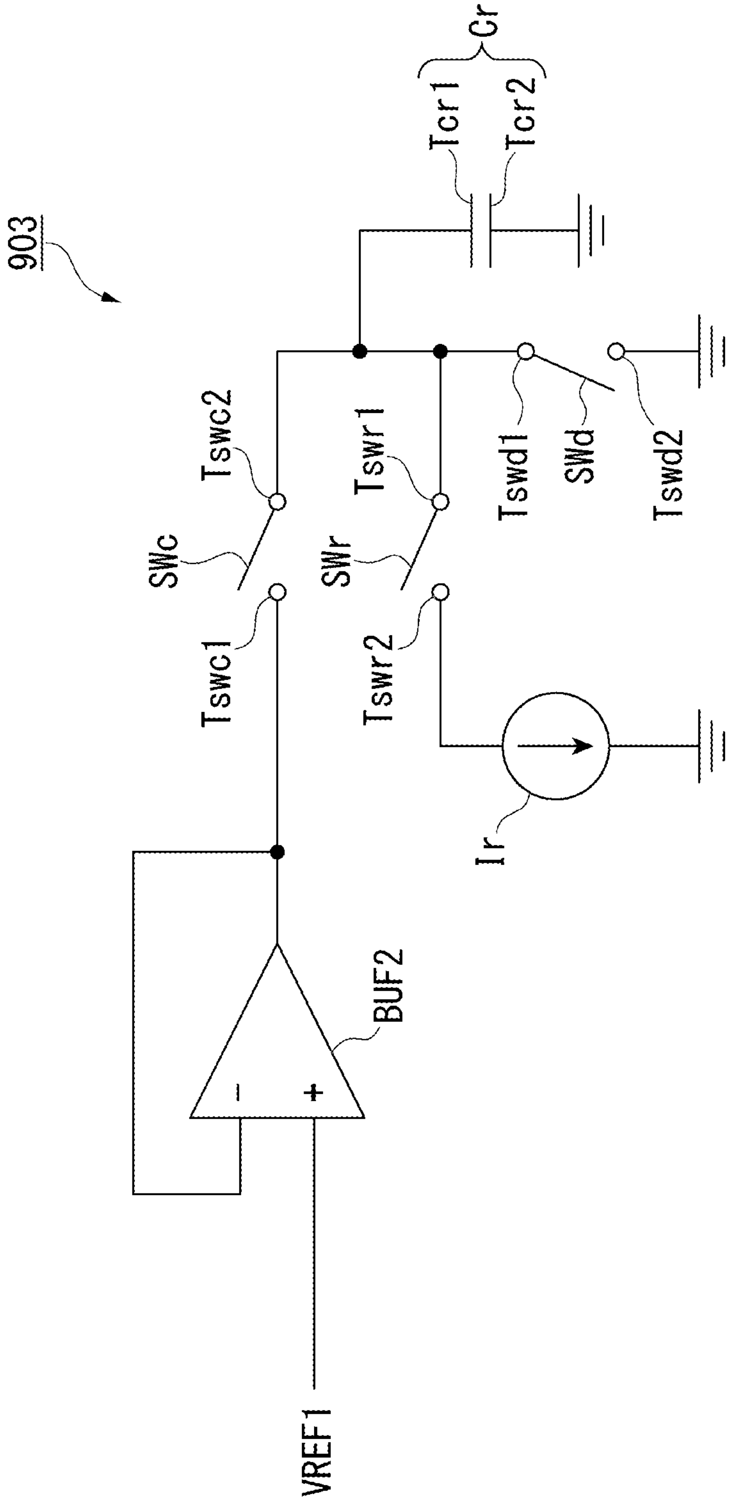
FIG. 6 is a diagram showing a configuration of a reference signal generation circuit in the image sensor included in the endoscope system according to the first embodiment of the present invention.

FIG. 6 shows a configuration of the reference signal generation circuit 903. The reference signal generation circuit 903 includes a buffer BUF2, a switch SWc, a switch SWr, a switch SWd, a capacitance element Cr, and a current source Ir. The state of each switch shown in FIG. 6 becomes either an ON state or an OFF state. Each switch can switch between the ON state and the OFF state.

An analog voltage (VREF1) is generated by the voltage generation circuit 911 and is input to the buffer BUF2. The buffer BUF2 outputs the analog voltage.

The switch SWc includes a first terminal Tswc1 and a second terminal Tswc2. The first terminal Tswc1 of the switch SWc is connected to the buffer BUF2.

The capacitance element Cr includes a first terminal Tcr1 and a second terminal Tcr2. The first terminal Tcr1 of the capacitance element Cr is connected to the second terminal Tswc2 of the switch SWc. The second terminal Tcr2 of the capacitance element Cr is connected to the ground terminal 94. A ground voltage, which is lower than the analog voltage generated by the voltage generation circuit 911, is input to the second terminal Tcr2 of the capacitance element Cr.

When the state of the switch SWc is the ON state, the analog voltage output from the buffer BUF2 is input to the first terminal Tcr1 of the capacitance element Cr via the switch SWc. The capacitance element Cr holds the analog voltage.

The switch SWr includes a first terminal Tswr1 and a second terminal Tswr2. The first terminal Tswr1 of the switch SWr is connected to the second terminal Tswc2 of the switch SWc and the first terminal Tcr1 of the capacitance element Cr. The second terminal Tswr2 of the switch SWr is connected to the current source Ir.

The switch SWd is a voltage adjustment circuit that adjusts an analog voltage provided to the reference signal generation circuit 903. The switch SWd includes a first terminal Tswd1 and a second terminal Tswd2. The first terminal Tswd1 of the switch SWd is connected to the second terminal Tswc2 of the switch SWc and the first terminal Tcr1 of the capacitance element Cr. The second terminal Tswd2 of the switch SWd is connected to the ground terminal 94. The ground voltage is input to the second terminal Tswd2 of the switch SWd.

In the sampling period, the state of the switch SWc is set to the ON state, the state of the switch SWr is set to the OFF state, and the state of the switch SWd is set to the OFF state. At this time, the capacitance element Cr holds the analog voltage output from the buffer BUF2.

At a predetermined timing in the sampling period, the state of the switch SWc changes to the OFF state. Thereafter, the state of the switch SWd changes to the ON state. At this time, the switch SWd short-circuits the first terminal Tcr1 of the capacitance element Cr and the ground terminal 94. A short-circuit current flows through the switch SWd, and the voltage of the first terminal Tcr1 of the capacitance element Cr sharply decreases. The value of the short-circuit current is the same as that of current that flows through the counter 905. For example, a value of a current that flows through the switch SWd is the same as that of current that flows through the counter 905. Alternatively, a resistor may be connected to the switch SWd, and a value of a current that flows through the resistor may be the same as that of the current that flows through the counter 905.

After the voltage of the first terminal Tcr1 of the capacitance element Cr changes toward the ground voltage, the state of the switch SWd changes to the OFF state. At this time, the short-circuit connection between the first terminal Tcr1 of the capacitance element Cr and the ground terminal 94 is canceled.

After the state of the switch SWd changes to the OFF state, the state of the switch SWc changes to the ON state. At this time, the capacitance element Cr holds the analog voltage output from the buffer BUF2 again. The analog voltage is used for generating the reference signal in the AD conversion period.

Thereafter, the state of the switch SWc changes to the OFF state, and the sampling period is completed. The state of the switch SWr changes to the ON state, and the AD conversion period is started.

In the AD conversion period, the state of the switch SWc is the OFF state, the state of the switch SWr is the ON state, and the state of the switch SWd is the OFF state. At this time, a current flows through the switch SWr, and the voltage of the first terminal Tcr1 of the capacitance element Cr gradually decreases. The reference signal generation circuit 903 outputs the voltage of the first terminal Tcr1 of the capacitance element Cr as the reference signal.

Figure 7:
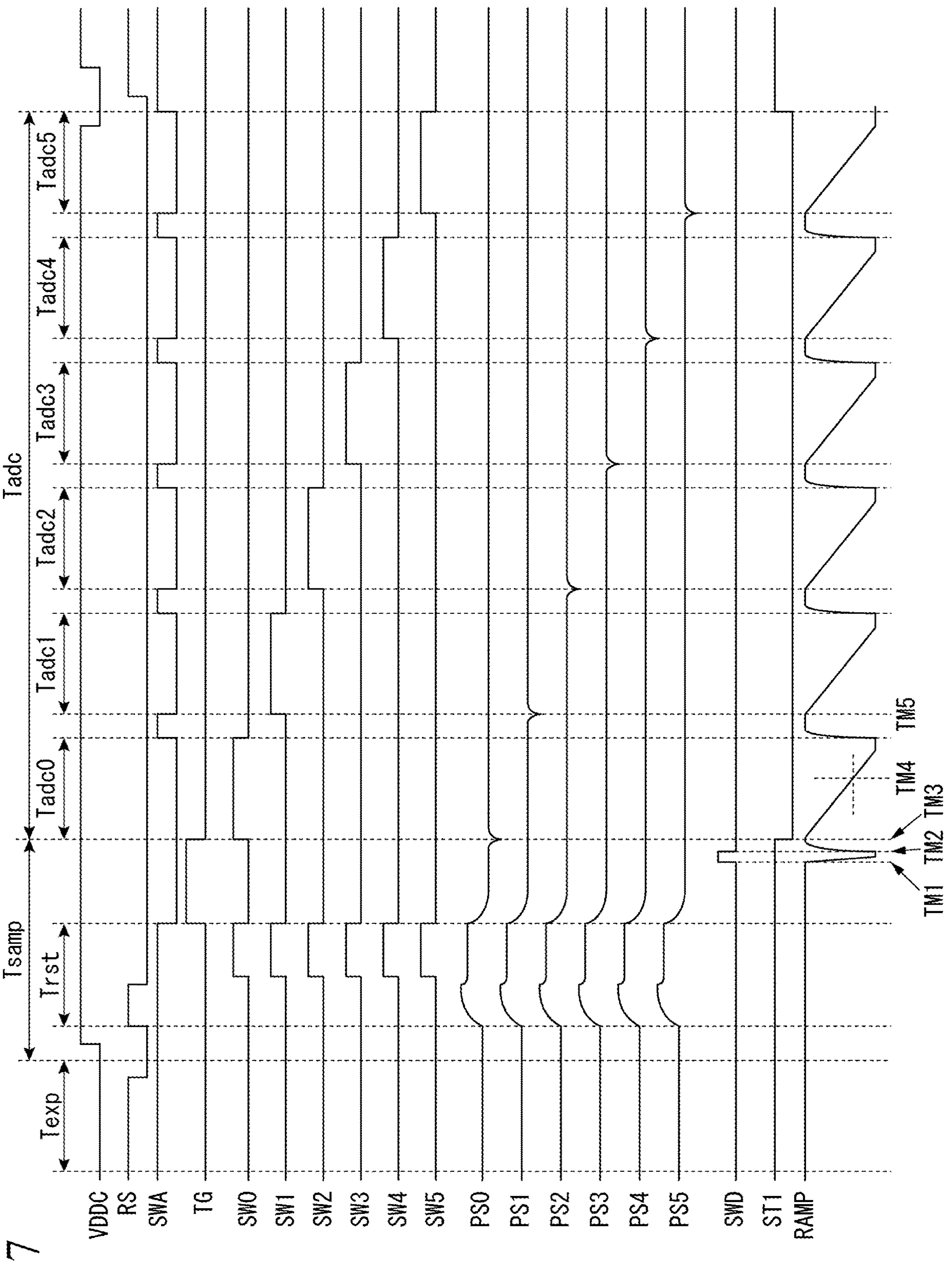
FIG. 7 is a timing chart showing waveforms of signals in the image sensor included in the endoscope system according to the first embodiment of the present invention.

FIG. 7 shows waveforms of a control signal VDDC, a control signal RS, a control signal SWA, a control signal TG, control signals SWO to SW5, pixel signals PSO to PS5, a control signal SWD, a start signal ST1, and a reference signal RAMP. The horizontal direction in FIG. 7 indicates time, and the vertical direction in FIG. 7 indicates a voltage value of each signal. An operation of the image sensor 90 will be described by using FIG. 7.

The control signal VDDC is input to a pixel PIX. The control signal RS is used for controlling the reset transistor RT of the pixel PIX. The control signal SWA is used for controlling the switch SWa of a reading circuit 902. The control signal TG is used for controlling the transfer transistor TT of the pixel PIX. The control signals SWO to SW5 are used for controlling the switches SW10 to SW15 and the switches SW20 to SW25 of the reading circuit 902. The pixel signals PSO to PS5 are output from pixels PIX of six columns.

The control signal SWD is used for controlling the switch SWd of the reference signal generation circuit 903. The start signal ST1 is input to the NOR circuit NOR1. The reference signal generation circuit 903 generates the reference signal RAMP. The voltage of the reference signal RAMP indicates the voltage of the first terminal Tcr1 of the capacitance element Cr. Each of the control signal VDDC, the control signal RS, the control signal SWA, the control signal TG, the control signals SWO to SW5, the control signal SWD, and the start signal ST1 has the H voltage or the L voltage.

In an exposure period Texp, the voltage of the control signal VDDC is the L voltage. The control signal VDDC is used for selecting pixels PIX of one row. The pixels PIX to which the control signal VDDC having the L voltage is input are not selected. The voltage of the control signal VDDC is set to the L voltage in order to prevent the pixels PIX that are not selected from outputting pixel signals. In the exposure period Texp, the photoelectric conversion unit PD generates an electric charge in accordance with the amount of light incident thereon.

Thereafter, a sampling period Tsamp is started. The sampling period Tsamp includes a reset period Trst. Before the reset period Trst is started, the voltage of the control signal VDDC is set to the H voltage and the voltage of the control signal RS is set to the H voltage. In the sampling period Tsamp and an AD conversion period Tade described later, the voltage of the control signal VDDC is maintained to be the H voltage and the pixel PIX is selected. When the voltage of the control signal RS is the H voltage, the reset transistor RT resets the voltage of the charge storage portion FD to a voltage in accordance with the control signal VDDC.

In the reset period Trst, the voltages of the control signals SWO to SW5 are set to the H voltage. The state of each of the switches SW10 to SW15 and SW20 to SW25 in the reading circuit 902 is set to the ON state. The output transistor OT of each of the pixels PIX of six columns outputs a pixel signal corresponding to the first pixel signal to the vertical signal line VL based on the voltage of the charge storage portion FD.

In one of the reading circuits 902, the pixel signal PSO is input to the capacitance element C0 via the switch SW10. The capacitance element C0 holds an analog signal corresponding to the pixel signal PSO. In the other five reading circuits 902, the capacitance elements C1 to C5 similarly hold analog signals corresponding to the pixel signals PSI to PS5. Thereafter, the voltages of the control signals SWO to SW5 are set to the L voltage, and the reset period Trst is completed. The state of each of the switches SW10 to SW15 and SW20 to SW25 changes to the OFF state.

In the exposure period Texp and the reset period Trst, the capacitance element Cr of the reference signal generation circuit 903 holds the analog voltage generated by the voltage generation circuit 911. The reference signal generation circuit 903 outputs the analog voltage to the comparator 904.

The voltage of the control signal SWA is the H voltage and the state of the switch SWa is maintained to be the ON state until the reset period Trst is completed. When the state of each of the switches SW10 to SW15 and SW20 to SW25 of the reading circuit 902 is the ON state, the analog voltage input from the reference signal generation circuit 903 to the non-inverting input terminal IN2 of the comparison circuit COMP is output from the output terminal OUT1 of the comparison circuit COMP to the capacitance elements C0 to C5 via the switch SWa and the switches SW20 to SW25. In order for each of the capacitance elements C0 to C5 to hold the analog signal corresponding to the first pixel signal, the analog voltage generated by the reference signal generation circuit 903 needs to be output to the capacitance elements C0 to C5. When the reset period Trst is completed, the voltage of the control signal SWA is set to the L voltage and the state of the switch SWa changes to the OFF state.

In the sampling period Tsamp after the reset period Trst is completed, the voltage of the control signal TG is set to the H voltage. The transfer transistor TT of each of the pixels PIX of six columns transfers the electric charge generated by the photoelectric conversion unit PD to the charge storage portion FD. The voltage of the charge storage portion FD decreases. The output transistor OT of each of the pixels PIX of six columns outputs a pixel signal corresponding to the second pixel signal to the vertical signal line VL based on the voltage of the charge storage portion FD. The voltage of the second pixel signal is lower than that of the first pixel signal.

In one of the reading circuits 902, the pixel signal PSO is input to the capacitance element C0 via the switch SW10. The capacitance element C0 holds an analog signal corresponding to the difference between the first pixel signal and the second pixel signal. In the other five reading circuits 902, each of the capacitance elements C1 to C5 similarly holds an analog signal corresponding to the difference between the first pixel signal and the second pixel signal.

Thereafter, the voltage of the control signal TG is set to the L voltage. The voltage of the control signal SWD is set to the H voltage at a timing TM1, and the state of the switch SWd of the reference signal generation circuit 903 changes to the ON state. The first terminal Tcr1 of the capacitance element Cr of the reference signal generation circuit 903 and the ground terminal 94 are short-circuited, and the voltage of the first terminal Tcr1 of the capacitance element Cr sharply decreases. After the voltage of the first terminal Tcr1 of the capacitance element Cr changes toward the ground voltage, the voltage of the control signal SWD is set to the L voltage at a timing TM2. The state of the switch SWd changes to the OFF state, and the short-circuit connection between the first terminal Tcr1 of the capacitance element Cr and the ground terminal 94 is canceled. After the state of the switch SWd changes to the OFF state, the capacitance element Cr holds the analog voltage generated by the voltage generation circuit 911.

In the exposure period Texp and the sampling period Tsamp, the voltage of the start signal ST1 is set to the H voltage. After the state of the switch SWd changes to the OFF state, the voltage of the start signal ST1 is set to the L voltage. At this time, the sampling period Tsamp is completed, and the AD conversion period Tade is started.

The AD conversion period Tade includes AD conversion periods Tadc0 to Tadc5. In each of the AD conversion periods Tadc0 to Tadc5, the analog signal held by any one of the capacitance elements C0 to C5 is input to the inverting input terminal IN1 of the comparison circuit COMP via any one of the switches SW20 to SW25. In each of the AD conversion periods Tadc0 to Tadc5, the reference signal RAMP is output from the reference signal generation circuit 903 and is input to the non-inverting input terminal IN2 of the comparison circuit COMP. In each of the AD conversion periods Tadc0 to Tadc5, the comparison circuit COMP compares the voltage of the inverting input terminal IN1 with the voltage of the non-inverting input terminal IN2.

An operation of the image sensor 90 in the AD conversion period Tadc0 will be described. At a timing TM3 at which the AD conversion period Tadc0 is started, the state of the switch SWr of the reference signal generation circuit 903 changes to the ON state. A current flows through the switch SWr, and the voltage of the first terminal Tcr1 of the capacitance element Cr gradually decreases. The reference signal generation circuit 903 outputs the reference signal RAMP having the voltage that gradually decreases to the comparator 904. The reference signal RAMP is input to the non-inverting input terminal IN2 of the comparison circuit COMP.

The counter 905 starts an operation in the timing TM3. The voltage of the control signal SWO is set to the H voltage at the timing TM3. The state of each of the switches SW10 and SW20 of the reading circuit 902 is set to the ON state. The analog signal held by the capacitance element C0 is input to the inverting input terminal IN1 of the comparison circuit COMP via the switch SW20.

The comparison circuit COMP compares the voltage of the inverting input terminal IN1 with the voltage of the non-inverting input terminal IN2 and outputs the comparison signal to the latch circuit 906. For example, at a timing TM4, the voltage of the non-inverting input terminal IN2 matches the voltage of the inverting input terminal IN1. In other words, the voltage of the reference signal RAMP matches the voltage of the analog signal held by the capacitance element C0. At this time, the voltage of the comparison signal changes, and the latch circuit 906 holds a digital value output from the counter 905. The digital value corresponds to the length of the period from the timing TM3 to the timing TM4. The length corresponds to the voltage of the analog signal held by the capacitance element C0.

Thereafter, the voltage of the control signal SWO is set to the L voltage, and the AD conversion period Tadc0 is completed. The counter 905 stops the operation. The capacitance element Cr of the reference signal generation circuit 903 holds the analog voltage generated by the voltage generation circuit 911.

At a timing TM5, the AD conversion period Tadc1 is started. An operation of the image sensor 90 in the AD conversion period Tadc1 is similar to that of the image sensor 90 in the AD conversion period Tadc0. After the AD conversion period Tadc1 is completed, the AD conversion periods Tade2 to Tadc5 are sequentially started. An operation of the image sensor 90 in each of the AD conversion periods Tadc2 to Tadc5 is similar to that of the image sensor 90 in the AD conversion period Tadc0.

An analog voltage is generated by the voltage generation circuit 911 and is provided to the reference signal generation circuit 903. The counter 905 operates in the AD conversion periods Tadc0 to Tadc5. Therefore, the amount of change of the analog voltage generated immediately before each of the AD conversion periods Tadc1 to Tadc5 is almost the same in the AD conversion periods Tadc1 to Tadc5.

While the counter 905 operates in the AD conversion periods Tadc0 to Tadc5, the analog voltage changes. The counter 905 does not operate immediately before each of the AD conversion periods Tadc1 to Tadc5. However, since the interval between two consecutive AD conversion periods is short, the change of the analog voltage in each of the AD conversion periods Tadc0 to Tadc4 still remains immediately before each of the AD conversion periods Tadc1 to Tadc5.

The switch SWd of the reference signal generation circuit 903 short-circuits the first terminal Tcr1 of the capacitance element Cr and the ground terminal 94 immediately before the AD conversion period Tadc0. Although the counter 905 stops immediately before the AD conversion period Tadc0, the reference signal generation circuit 903 consumes the same amount of current as that of current consumed by the counter 905. Therefore, the amount of change of the analog voltage generated immediately before the AD conversion period Tadc0 is almost the same as that of change of the analog voltage generated in the AD conversion period Tadc0 during which the counter 905 operates. The voltage of the reference signal RAMP at the timing TM3 of the AD conversion period Tadc0 is almost the same as that of the reference signal RAMP at the timing TM5 of the AD conversion period Tadc1.

Since the switch SWd of the reference signal generation circuit 903 short-circuits the first terminal Tcr1 of the capacitance element Cr and the ground terminal 94, the voltage of the reference signal RAMP at the timing TM3 of the AD conversion period Tadc0 is different from that of the reference signal RAMP in the exposure period Texp or the reset period Trst. A first difference (absolute value) is less than a second difference (absolute value). The first difference indicates a difference between the voltage of the reference signal RAMP at the timing TM3 of the AD conversion period Tadc0 and the voltage of the reference signal RAMP at the timing TM5 of the AD conversion period Tadc1. The second difference indicates a difference between the voltage of the reference signal RAMP in the exposure period Texp or the reset period Trst and the voltage of the reference signal RAMP at the timing TM5 of the AD conversion period Tade1.

An error of the voltage of the reference signal RAMP at the timing at which the AD conversion period Tadc0 is started is reduced. Therefore, the image sensor 90 can execute AD conversion with high accuracy.

The reference signal generation circuit 903 may generate a reference signal that gradually increases. In such a case, the polarity of transistors included in the pixel unit 900, the reading circuit 902, the reference signal generation circuit 903, and the like is changed. In such a case, an analog voltage corresponding to the ground voltage is provided to the reference signal generation circuit 903. In such a case, the ground terminal 94 is changed to a voltage terminal to which the power source voltage is provided.

Figure 8:
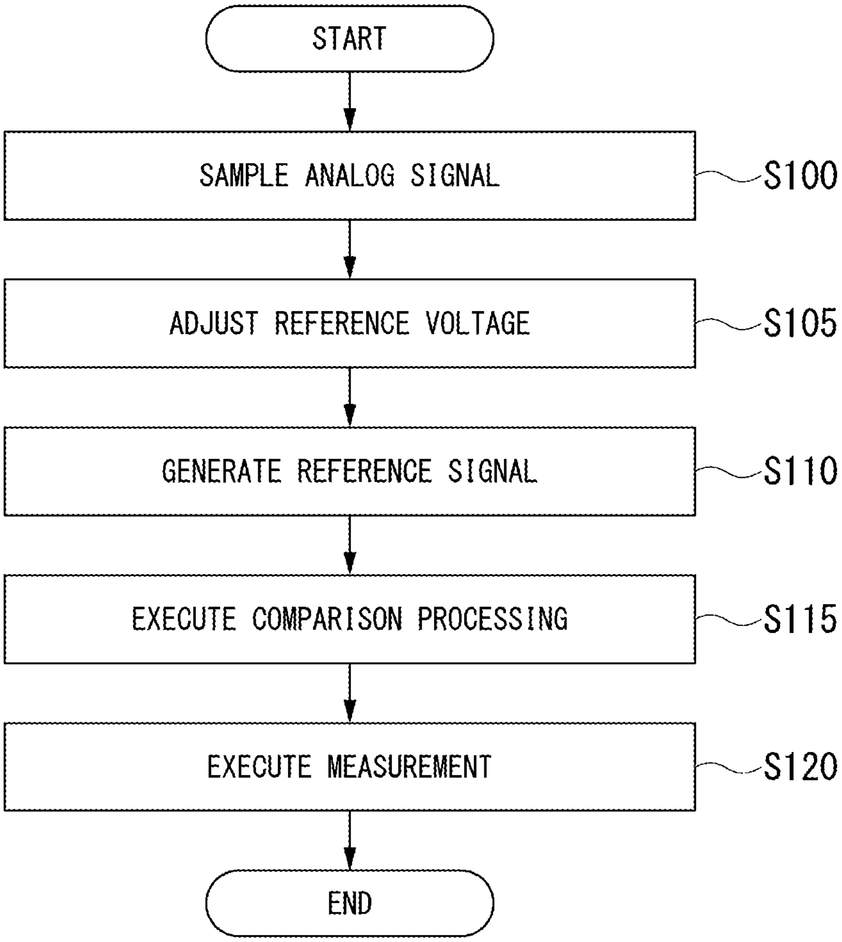
FIG. 8 is a flow chart showing a signal-processing method according to the first embodiment of the present invention.

FIG. 8 shows a signal-processing method according to each aspect of the present invention. The reading circuit 902 (sampling circuit) samples an analog signal output from each of pixels PIX disposed in a predetermined number of columns in a sampling period. The predetermined number is at least two. The reading circuit 902 samples the predetermined number of analog signals in the sampling period (Step S100).

The switch SWd (voltage adjustment circuit) of the reference signal generation circuit 903 adjusts an analog voltage provided to the reference signal generation circuit 903 before a first timing (timing TM3) of a first period (AD conversion period Tadc0). Specifically, the switch SWd adjusts the analog voltage such that a value of a first voltage of the reference signal RAMP at the first timing of the first period nears a value of a second voltage at a first timing (timing TM5) of a second period (AD conversion period Tadc1) (Step S105). The first period is a reference signal generation period immediately after the sampling period Tsamp. The second period is a reference signal generation period after the first period.

The reference signal generation circuit 903 generates the reference signal RAMP having a voltage that gradually increases or decreases from the first timing by using the analog voltage in a reference signal generation period. Specifically, the reference signal generation circuit 903 generates the reference signal RAMP having the first voltage at the first timing (timing TM3) of the first period (AD conversion period Tadc0). In addition, the reference signal generation circuit 903 generates the reference signal RAMP having the second voltage at the first timing (timing TM5) of the second period (AD conversion period Tadc1) (Step S110).

The comparator 904 executes comparison processing of comparing the voltage of the analog signal sampled by the reading circuit 902 with the voltage of the reference signal RAMP. At this time, the comparator 904 compares the voltage of each of the predetermined number of analog signals with the voltage of the reference signal RAMP, thus executing the comparison processing the same number of times as the predetermined number (Step S115).

The counter 905 (measurement circuit) measures the length of a period from the first timing (timing TM3) to a second timing (timing TM4) at which the voltage of the analog signal and the voltage of the reference signal RAMP match each other (Step S120). Steps S110 to S120 are executed the same number of times as the predetermined number.

Each aspect of the present invention may include the following modified example. The switch SWd (voltage adjustment circuit) short-circuits the reference signal generation circuit 903 and the ground terminal 94 (voltage terminal) at a third timing (timing TM1) before a first period (AD conversion period Tadc0). A different ground voltage from an analog voltage generated by the voltage generation circuit 911 is provided to the ground terminal 94. The switch SWd cancels a short circuit between the reference signal generation circuit 903 and the ground terminal 94 at a fourth timing (timing TM2) that occurs after the third timing and before the first period. The switch SWd adjusts the analog voltage by executing the operation like this.

In an example in which the voltage of the reference signal gradually decreases, a lower voltage (for example, the ground voltage) than the analog voltage generated by the voltage generation circuit 911 is provided to the voltage terminal of the reference signal generation circuit 903. In an example in which the voltage of the reference signal gradually increases, a higher voltage (for example, the power source voltage) than the analog voltage generated by the voltage generation circuit 911 is provided to the voltage terminal of the reference signal generation circuit 903.

Each aspect of the present invention may include the following modified example. The reference signal generation circuit 903 includes the capacitance element Cr that holds the first voltage and the second voltage. The switch SWd (voltage adjustment circuit) short-circuits the capacitance element Cr and the ground terminal 94 (voltage terminal) at the third timing (timing TM1) and cancels a short circuit between the capacitance element Cr and the ground terminal 94 at the fourth timing (timing TM2).

Each aspect of the present invention may include the following modified example. The third timing (timing TM1) occurs after the pixels PIX are reset and before the first timing (timing TM3) of the first period (AD conversion period Tadc0).

Each aspect of the present invention may include the following modified example. The reference signal generation circuit 903 outputs the reference signal RAMP having a third voltage in a third period (the exposure period Texp or the reset period Trst). The third period is included in the sampling period Tsamp and occurs before a period during which the switch SWd (voltage adjustment circuit) adjusts the analog voltage. The difference between the first voltage and the second voltage is less than that between the third voltage and the second voltage.

In the first embodiment, the image sensor 90 can execute AD conversion with high accuracy.

Second Embodiment

Figure 9:
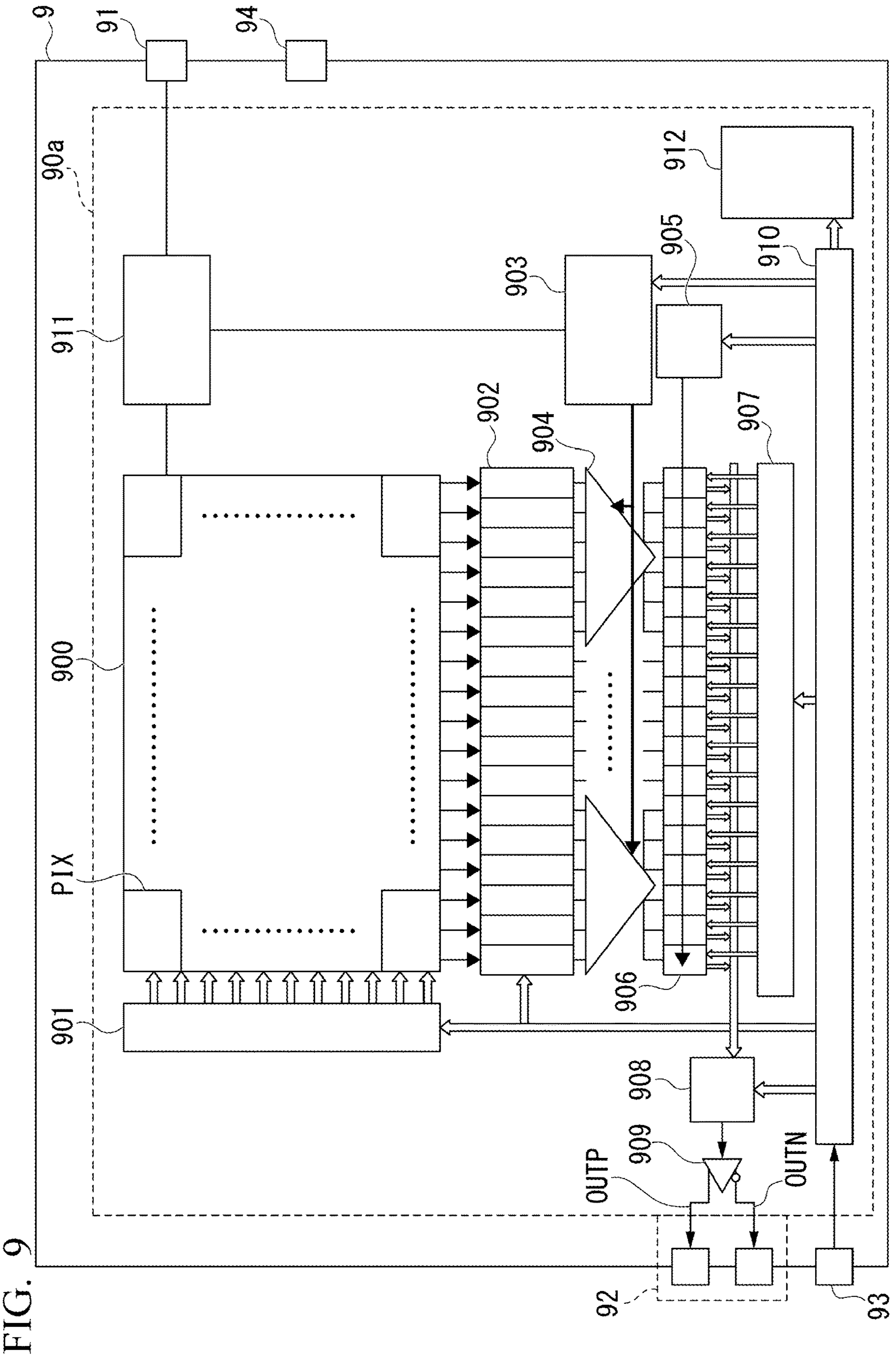
FIG. 9 is a block diagram showing a configuration of an image sensor included in an endoscope system according to a second embodiment of the present invention.

A second embodiment of the present invention will be described. The image sensor 90 shown in FIG. 3 is changed to an image sensor 90*a* shown in FIG. 9. FIG. 9 shows a configuration of the image sensor 90*a*. The image sensor 90*a* includes a pixel unit 900, a reading control unit 901, a reading circuit 902, a reference signal generation circuit 903, a comparator 904, a counter 905, a latch circuit 906, a horizontal reading control unit 907, a digital signal-processing unit 908, a signal output unit 909, a TG 910, a voltage generation circuit 911, and a current circuit 912. The description of the same configuration as that shown in FIG. 3 will be omitted.

The reference signal generation circuit 903 does not include the switch SWd shown in FIG. 6. Alternatively, the state of the switch SWd is maintained to be the OFF state while the image sensor 90*a* operates.

The current circuit 912 consumes the same amount of current as that of current consumed by the counter 905. The current circuit 912 is a voltage adjustment circuit that adjust an analog voltage provided to the reference signal generation circuit 903.

Figure 10:
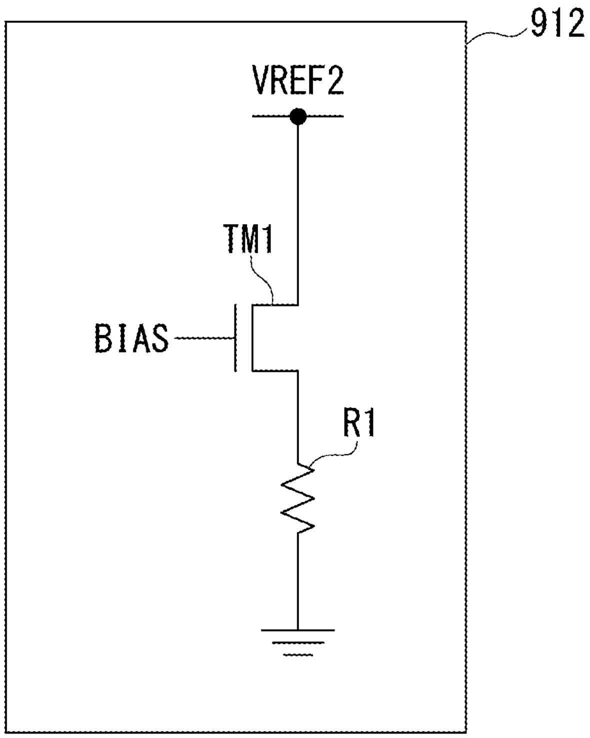
FIG. 10 is a diagram showing a configuration of a current circuit in the image sensor included in the endoscope system according to the second embodiment of the present invention.

FIG. 10 shows a configuration of the current circuit 912. The current circuit 912 includes a transistor TM1 and a resistor R1.

An analog voltage (VREF2) is generated by the voltage generation circuit 911 and is input to the drain terminal of the transistor TM1. The power source voltage transferred by the power source line 30 may be input to the drain terminal of the transistor TM1. The resistor R1 is connected to the source terminal of the transistor TM1 and the ground terminal 94.

A control signal BIAS is generated by the TG 910 and is input to the gate terminal of the transistor TM1. The state of the transistor TM1 becomes either an ON state or an OFF state in accordance with the control signal BIAS. The control signal BIAS has the H voltage or the L voltage. When the voltage of the control signal BIAS is the H voltage, the state of the transistor TM1 is the ON state. When the voltage of the control signal BIAS is the L voltage, the state of the transistor TM1 is the OFF state.

When the state of the transistor TM1 is the ON state, a predetermined current flows through the transistor TM1 and the resistor R1. The resistance value of the resistor R1 is set such that the same amount of current as that of current flowing through the counter 905 flows through the transistor TM1 and the resistor R1. When the state of the transistor TM1 is the OFF state, the above-described current is stopped.

The resistor R1 has a fixed resistance value. The resistance value of the resistor R1 may be variable. The power source voltage and the like transferred by the power source line 30 may change in accordance with the temperature and the like, and a current flowing through the counter 905 may change. In order to adjust the current consumption of the current circuit 912 in accordance with a change of the current, the resistance value of the resistor R1 may be controlled in accordance with the temperature and the like.

The current circuit 912 is connected to the ground terminal 94. The reference signal generation circuit 903 shown in FIG. 6 is also connected to the ground terminal 94. The current circuit 912 and the reference signal generation circuit 903 are connected in parallel to the ground terminal 94 to which the analog voltage generated by the voltage generation circuit 911 is provided.

Figure 11:
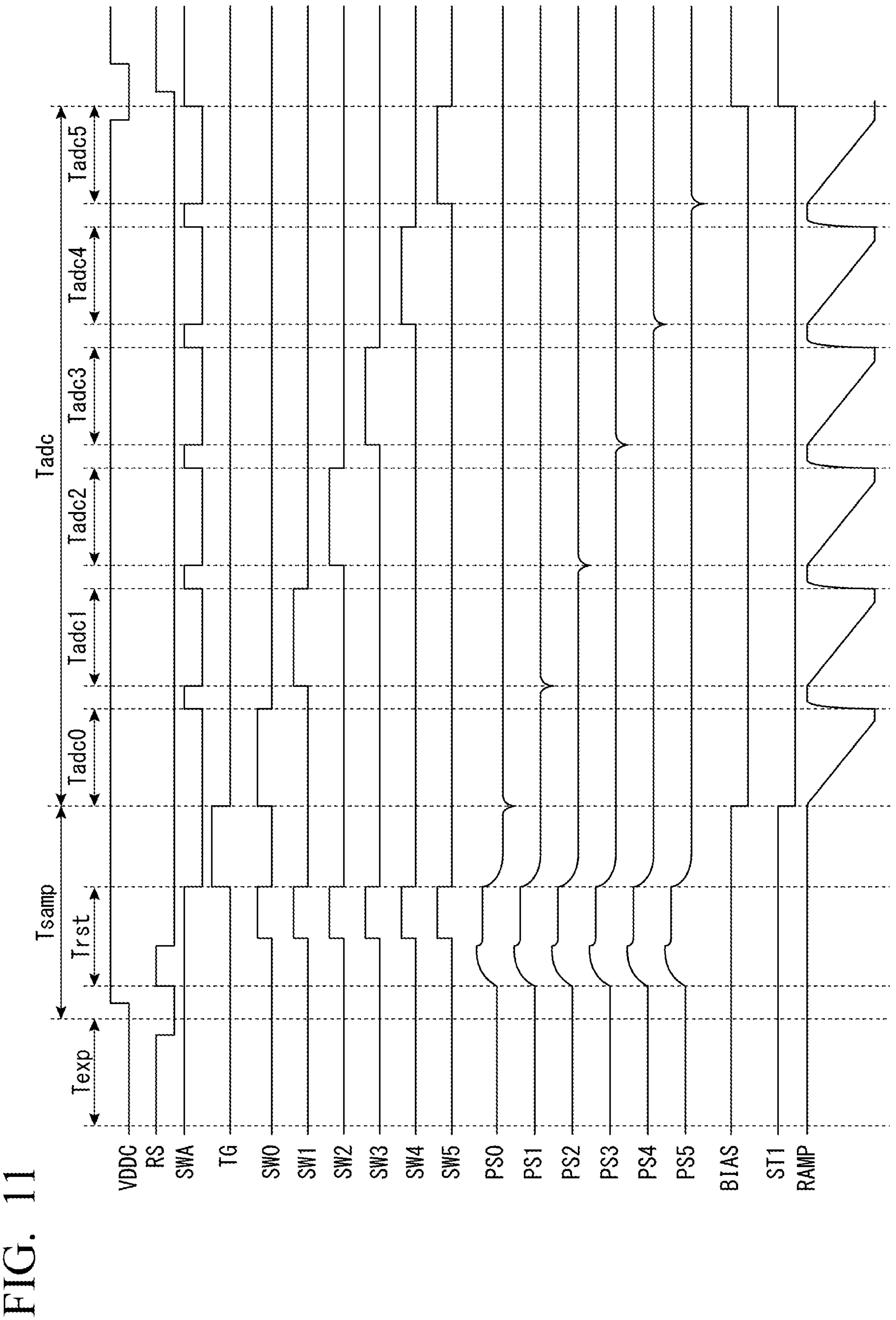
FIG. 11 is a timing chart showing waveforms of signals in the image sensor included in the endoscope system according to the second embodiment of the present invention.

FIG. 11 shows waveforms of a control signal VDDC, a control signal RS, a control signal SWA, a control signal TG, control signals SWO to SW5, pixel signals PSO to PS5, a control signal BIAS, a start signal ST1, and a reference signal RAMP. The horizontal direction in FIG. 11 indicates time, and the vertical direction in FIG. 11 indicates a voltage value of each signal. An operation of the image sensor 90*a* will be described by using FIG. 11. The descriptions of the same parts as those shown in FIG. 7 will be omitted.

The control signal BIAS is input to the gate terminal of the transistor TM1 of the current circuit 912. In an exposure period Texp and a sampling period Tsamp, the voltage of the control signal BIAS is the H voltage. Therefore, the state of the transistor TM1 is the ON state, and the current circuit 912 consumes the same amount of current as that of current consumed by the counter 905.

At a timing at which the sampling period Tsamp is completed, the voltage of the control signal BIAS changes to the L voltage. Therefore, the state of the transistor TM1 changes to the OFF state, and the current circuit 912 stops consumption of the current. In an AD conversion period Tadc following the sampling period Tsamp, the voltage of the control signal BIAS is the L voltage.

An analog voltage is generated by the voltage generation circuit 911 and is provided to the reference signal generation circuit 903. In the exposure period Texp and the sampling period Tsamp, the capacitance element Cr of the reference signal generation circuit 903 holds the analog voltage. The reference signal generation circuit 903 outputs the analog voltage to the comparator 904.

The counter 905 operates in AD conversion periods Tadc0 to Tadc5. Therefore, the amount of change of the analog voltage generated immediately before each of the AD conversion periods Tadc1 to Tadc5 is almost the same in the AD conversion periods Tade1 to Tadc5.

While the counter 905 operates in the AD conversion periods Tadc0 to Tadc5, the analog voltage changes. The counter 905 does not operate immediately before each of the AD conversion periods Tadc1 to Tadc5. However, since the interval between two consecutive AD conversion periods is short, the change of the analog voltage in each of the AD conversion periods Tadc0 to Tadc4 still remains immediately before each of the AD conversion periods Tadc1 to Tadc5.

Although the counter 905 stops immediately before the AD conversion period Tadc0, the current circuit 912 consumes the same amount of current as that of current consumed by the counter 905. Therefore, the amount of change of the analog voltage generated immediately before the AD conversion period Tadc0 is almost the same as that of change of the analog voltage generated in the AD conversion period Tadc0 during which the counter 905 operates. The voltage of the reference signal RAMP at a timing at which the AD conversion period Tadc0 is started is almost the same as that of the reference signal RAMP at a timing at which the AD conversion period Tadc1 is started.

Each aspect of the present invention may include the following modified example. The current circuit 912 (voltage adjustment circuit) adjusts the analog voltage at a first timing (timing TM3) of a first period (AD conversion period Tadc0) by consuming the same amount of current as that of current consumed by the counter 905 (measurement circuit) before the first period.

Each aspect of the present invention may include the following modified example. The current circuit 912 (voltage adjustment circuit) and the reference signal generation circuit 903 are connected in parallel to the ground terminal 94 (voltage terminal) to which the analog voltage is provided.

In the second embodiment, the image sensor 90*a* can execute AD conversion with high accuracy.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device, comprising:

pixels disposed in a matrix shape having two or more rows and two or more columns;

a sampling circuit configured to sample an analog signal output from each of the pixels disposed in a multiple predetermined number of the columns in a sampling period;

a reference signal generation circuit configured to generate a reference signal having a voltage that gradually increases or decreases from a first timing by using an analog voltage in a reference signal generation period;

a comparator configured to execute comparison processing of comparing a voltage of the analog signal sampled by the sampling circuit with a voltage of the reference signal;

a measurement circuit configured to measure a length of a period from the first timing to a second timing at which the voltage of the analog signal and the voltage of the reference signal match each other; and a voltage adjustment circuit, wherein the sampling circuit is configured to sample the predetermined number of the analog signals in the sampling period, wherein the reference signal generation circuit is configured to generate the reference signal having a first voltage at the first timing of a first period that is the reference signal generation period immediately after the sampling period and is configured to generate the reference signal having a second voltage at the first timing of a second period that is the reference signal generation period after the first period, wherein the voltage adjustment circuit is configured to adjust the analog voltage provided to the reference signal generation circuit before the first timing of the first period, wherein the comparator is configured to compare the voltage of each of the analog signals with the voltage of the reference signal changing from the first voltage so as to execute the comparison processing in the first period and compare the voltage of each of the analog signals with the voltage of the reference signal changing from the second voltage so as to execute the comparison processing in the second period, and wherein the voltage adjustment circuit is configured to short-circuit, at a third timing before the first period, the reference signal generation circuit and a voltage terminal to which a different voltage from the analog voltage is provided and is configured to cancel a short circuit between the reference signal generation circuit and the voltage terminal at a fourth timing that occurs after the third timing and before the first period so as to adjust the analog voltage.

2. The imaging device according to claim 1 wherein the reference signal generation circuit includes a capacitance element configured to hold the first voltage and the second voltage, and wherein the voltage adjustment circuit is configured to short-circuit the capacitance element and the voltage terminal at the third timing and is configured to cancel a short circuit between the capacitance element and the voltage terminal at the fourth timing.

3. The imaging device according to claim 2, wherein the third timing occurs after the pixels are reset and before the first timing of the first period.

4. The imaging device according to claim 1, wherein the voltage adjustment circuit is configured to adjust the analog voltage by consuming the same amount of current as an amount of current consumed by the measurement circuit before the first period.

5. The imaging device according to claim 4, wherein the voltage adjustment circuit and the reference signal generation circuit are connected in parallel to a voltage terminal to which the analog voltage is provided.

6. The imaging device according to claim 1,
wherein the reference signal generation circuit is configured to output the reference signal having a third voltage in a third period,
wherein the third period is included in the sampling period and occurs before a period during which the voltage adjustment circuit adjusts the analog voltage, and
wherein a difference between the first voltage and the second voltage is less than a difference between the third voltage and the second voltage.

7. An endoscope system, comprising
a scope to be inserted into a living body; and
the imaging device according to claim 1,
wherein the imaging device is disposed in a distal end of the scope.

8. A signal-processing method, comprising:
a step in which a sampling circuit samples an analog signal output from each of pixels disposed in a multiple predetermined number of columns in a sampling period;
a step in which a reference signal generation circuit generates a reference signal having a voltage that gradually increases or decreases from a first timing by using an analog voltage in a reference signal generation period;
a step in which a comparator executes comparison processing of comparing a voltage of the analog signal sampled by the sampling circuit with a voltage of the reference signal;
a step in which a measurement circuit measures a length of a period from the first timing to a second timing at which the voltage of the analog signal and the voltage of the reference signal match each other; and
a step in which a voltage adjustment circuit adjusts the analog voltage provided to the reference signal generation circuit,
wherein the step of sampling the analog signal includes sampling the predetermined number of the analog signals in the sampling period,
wherein the step of comparing the voltage of the analog signal with the voltage of the reference signal includes comparing the voltage of each of the analog signals with the voltage of the reference signal so as to execute the comparison processing,
wherein the step of generating the reference signal includes generating the reference signal having a first voltage at the first timing of a first period that is the reference signal generation period immediately after the sampling period and includes generating the reference signal having a second voltage at the first timing of a second period that is the reference signal generation period after the first period,
wherein the step of adjusting the analog voltage includes adjusting the analog voltage provided to the reference signal generation circuit before the first timing of the first period,
wherein the step of comparing the voltage of the analog signal with the voltage of the reference signal includes comparing the voltage of each of the analog signals with the voltage of the reference signal changing from the first voltage so as to execute the comparison processing in the first period and comparing the voltage of each of the analog signals with the voltage of the reference signal changing from the second voltage so as to execute the comparison processing in the second period, and
wherein the step of adjusting the analog voltage provided to the reference signal generation circuit includes short-circuiting, at a third timing before the first period, the reference signal generation circuit and a voltage terminal to which a different voltage from the analog voltage is provided and includes cancelling a short circuit between the reference signal generation circuit and the voltage terminal at a fourth timing that occurs after the third timing and before the first period so as to adjust the analog voltage.

9. The imaging device according to claim 2
wherein the voltage adjustment circuit is configured to short-circuit the capacitance element and a ground terminal at the third timing and is configured to cancel a short circuit between the capacitance element and the ground terminal at the fourth timing.

* * * * *